United States Patent [19]

Askew et al.

[11] Patent Number: 4,708,810

[45] Date of Patent: Nov. 24, 1987

[54] OXIDATION RESISTANT COMPOSITION CONTAINING A BENZOTHIAZOLINE COMPOUND

[75] Inventors: Herbert F. Askew, Blunsdon; Paul R. Davies, Reading, both of United Kingdom

[73] Assignee: Castrol Limited, Wiltshire, England

[21] Appl. No.: 671,923

[22] Filed: Nov. 15, 1984

[30] Foreign Application Priority Data

Nov. 17, 1983 [GB] United Kingdom ............... 8330693

[51] Int. Cl.$^4$ .................. C07D 277/60; C09K 5/00; C10M 105/56
[52] U.S. Cl. ........................... 252/50; 252/51; 252/77; 548/152
[58] Field of Search ............... 548/152; 252/77, 50, 252/51

[56] References Cited

U.S. PATENT DOCUMENTS

| | | | |
|---|---|---|---|
| 3,513,237 | 5/1970 | Manning et al. | 548/152 X |
| 3,669,979 | 6/1972 | Freyermuth | 548/152 X |
| 3,912,606 | 10/1975 | Pacifici et al. | 548/152 X |
| 4,328,219 | 5/1982 | Mues et al. | 548/152 X |

Primary Examiner—John E. Kittle
Assistant Examiner—Mukund J. Shah
Attorney, Agent, or Firm—Bacon & Thomas

[57] ABSTRACT

Benzothiazoline derivatives having the general formula:

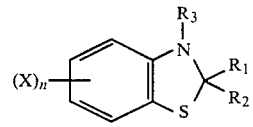

wherein $R_1$ and $R_2$ may be a hydrogen atom, a hydrocarbyl group, a substituted hydrocarbyl group, an amino group or a halogen atom, a hydroxyl group, alkoxy or aryloxy group, or $R_1$ and $R_2$ together may form a cyclic group which may optionally contain a heterocyclic atom; $R_3$ is a hydrogen atom or a hydrocarbyl group; X may be hydrocarbyl, substituted hydrocarbyl, halogen, hydroxyl, carboxyl, amino or amido two X's may be taken together to form a polycyclic compound which may be substituted in like manner; n=0 or 1-4 are useful as antioxidants for compounds subject to oxidative degradation. The compounds are prepared by reacting an appropriate o-aminothiophenol with a suitable carbonyl compound.

12 Claims, No Drawings

OXIDATION RESISTANT COMPOSITION CONTAINING A BENZOTHIAZOLINE COMPOUND

This invention relates to the use of benzothiazolines as antioxidants in compositions where improved oxidative stability is required such as in rubbers and polymers and plastics but in particular in functional fluids eg. lubricating oil compositions.

Many compounds have been proposed as antioxidants. Some of those used in the past have been unsatisfactory from a health and safety point of view. Many of such compounds have been corrosive and have had to be used in conjunction with corrosion inhibitors and metal deactivators. Furthermore, although prior art antioxidants have been effective in some lubricant base stocks, a change of base oil can render such antioxidants less effective.

The compounds of the present invention have been found to be useful as antioxidants in a wide range of compositions and are non-corrosive and additionally are believed to have a metal deactivating effect.

According to the present invention there is provided a composition comprising a constituent which may be subject to oxidative deterioration and a benzothiazoline derivative having the general formula:

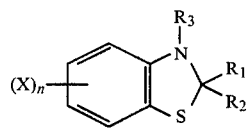

wherein $R_1$ and $R_2$ may be the same or different and may be a hydrogen atom, a hydrocarbyl group, a substituted hydrocarbyl group, an amino group or a halogen atom, a hydroxyl group, alkoxy or aryloxy group, or $R_1$ and $R_2$ together may form a cyclic group which may optionally contain a heterocyclic atom; $R_3$ is a hydrogen atom or a hydrocarbyl or substituted hydrocarbyl group; X is an optional substituent on the aromatic nucleus and where more than one substituent is present each may be the same or different and may be hydrocarbyl, halogen, hydroxyl, carboxyl, amino or amido or any other group which would not significantly impair the antioxidant properties of the compound; alternatively two substituents may be taken together to form a polycyclic compound which may be substituted by $(X)n$; n is zero or an integer of from 1 to 4.

Hydrocarbyl is defined as a group selected from alkyl, alkenyl, alkynyl, aryl, alkaryl, aralkyl or alicyclic.

The compounds used in the present invention may be used in a variety of compositions and the structure of the particular benzothiazoline may be tailored to suit the particular composition to be stabilised.

Thus in rubbers, plastics and polymers and co-polymers, whether they be addition or condensation polymers or co-polymers, the compounds of the present invention may be added to dry mixtures thereof during formulation, or in slightly larger amounts as free-radical eliminators and as antioxidants at the end of the polymerisation reaction.

The compounds are particularly useful in functional fluids such as lubricating oils, hydraulic oils and electrical oils and such oils may be based upon mineral or synthetic hydrocarbons, including polyalphaolefins or a wide variety of synthetic fluids which include carboxylate esters such as those used in gas turbine lubricants. They may also be used in fluids based on ethers or ether esters, glycols, glycol ethers, silicones, silicate esters or borate esters.

It is to be understood that such compositions may comprise, where necessary, additional antioxidants, corrosion inhibitors, lubricity agents, detergents, dispersants, vulcanisation and curing agents or any other additives normally used in the formulation of lubricants and plastics.

The compositions may contain up to 10% of the compounds above defined, although more generally amounts from 0.01% to 5% more particularly 0.1% to 2% by weight will be used.

The compounds may be prepared from an o-aminothiophenol and an appropriate carbonyl compound, optionally in the presence of a catalyst, preferably an acid catalyst, in accordance with the following equation.

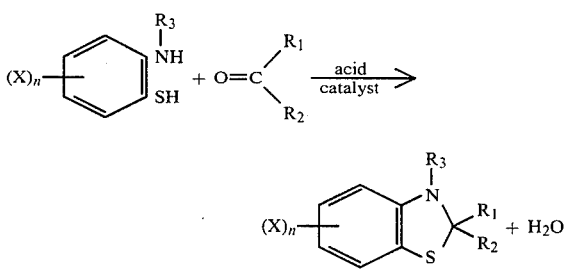

The reaction may be carried out at a temperature between ambient and 250° C. preferably 70° to 140° C. with the removal of water. The invention therefore includes a process so outlined.

Many carbonyl compounds may be used to prepare the benzothiazolines used in the present invention particularly useful examples of which are
methanal
ethanal
propanal
butanal
benzaldehyde
3,5 di-t-butyl-4-hydroxybenzaldehyde
propanone
4-methylpentan-2-one
butan-2-one
pentan-3-one
nonan-5-one
3-methylbutan-2-one
benzophenone
3, 3', 5, 5'-tetra-t-butyl-4-4'-dihydroxybenzophenone
cyclododecanone
4-methylcyclohexanone
4-t-butylcyclohexanone
anthrone
quinone
pyrrolidinone The o-aminothiophenol maybe prepared by sulphurising the appropriate amine as described in GB Patent No. 558887 There now follows by way of example typical preparations of compounds for use in accordance with the present invention and a demonstration of the effectiveness of the antioxidant and metal deactivation properties thereof.

Methods 1 and 2 give a detailed description of the preparation of 2,2-bisethylbenzothiazoline and 2,2- dimethylbenzothiazoline respectively using a catalyst. Method 3 gives a detailed description of the preparation of 2-phenylbenzothiazoline in the absence of a catalyst. The ingredients and results are tabulated in Table 1 together with the ingredients and results from substantially similar reactions and the results obtained from Rotary Bomb Tests (I.P. 229/73 tentative). When this test was carried out on the mineral oil the result was 20 minutes and on dioctylazelate the result was 9 minutes.

In this test 0.25% by weight of the product was dissolved in a medium viscosity mineral oil (150 solvent neutral) or 0.8% by weight in dioctyl azelate. The test oil (50+0.5 g) water (5 ml) and copper catalyst coil in a covered glass container was placed in a bomb equipped with a pressure gauge. The bomb was charged with oxygen to a pressure of 90 psi, (6.2 bar) placed in a constant temperature oil bath at 150° C. rotated axially at 100 rpm at an angle of 30 degrees from the horizontal. The test was terminated when the pressure dropped by 25 psi (1.72 bar) and the oxidation stability is assessed on the bomb life reported in minutes.

In order to demonstrate the corrosion inhibiting effects of some of the products, 1% by weight thereof were dissolved in the same mineral oil as above and the solutions were subject to a copper corrosion test known as IP154. The results of these tests are given under Test A in Table 2.

In order to demonstrate the metal deactivating effect of these compounds a stock solution of 0.1% weight of tetramethylthiuram disulphide in the same mineral oil was prepared to which was added 0.5% and 0.1% by weight of compounds in accordance with the present invention and subjected to the IP154 corrosion test. The results of these tests are given under Test B in Table 2.

In the IP154 test a polished copper strip is immersed in oil and heated at a selected temperature for a selected time. In this instance the temperature selected was 120° C. and the immersion time was three hours. At the end of the test the copper strip is removed, washed and compared with the ASTM copper strip corrosion standards. These are numbered from 1a (bright and clean) to 4c (black or worse).

The stock solution of 0.1% tetra-methylthiuram disulphide under the same conditions gave a result of 4c.

Full details of these tests can be found in the Institute of Petroleum Book of Test Methods.

METHOD 1

2-Aminothiophenol (25.0 g, 0.2 mole) and pentan-3-one (17.2 g, 0.2 Mole) in toluene (200 ml), together with Amberlyst 15 acid ion exchange resin (2 g) as catalyst were put in a 500 ml round bottomed flask fitted with a Dean & Stark trap and reflux condenser. The mixture was heated to reflux and water evolved by the reaction was collected in the Dean & Stark trap.

Water evolution ceased after 3.8 ml (Theory 3.6 ml) had been collected. After the mixture had cooled to ca 50° C. the mixture was filtered to remove the catalyst and the solvents removed in vacuo to yield a yellow oil. (Yield 34.10 g, 88%).

Found, N=6.86%; S=16.30%. $C_{11}H_{15}NS$ requires N=7.25%; S=16.58%.

METHOD 2

2-Aminothiophenol (50.0 g, 0.4 mole) and propan-2-one (58 g, 1.0 mole) in toluene (200 ml) were placed in a 500 ml round bottomed flask fitted with a Dean & Stark trap and reflux condenser; Amberlyst 15 acid ion exchange resin (5 g) was added to the solution as catalyst, and the mixture heated to reflux. A homogeneous azeotrope collected in the Dean & Stark trap. The distillate was drained from the trap regularly and when ca 40 ml had been drained water was observed to collect in the trap to a volume of 0.5 ml. Total reaction time was in the order of 2 hours. At the end of this time the solution was allowed to cool to ca 50° C. and then filtered to remove catalyst. The solvents were removed in vacuo to yield a free-flowing red oil which sometimes solidified to a red crystalline mass. (Yield, 60.32 g, 91%).

Found, N=8.24%; S=20.09%. $C_9H_{11}NS$ requires N=8.48%; S=19.39%.

METHOD 3

Benzaldehyde (10.6 g, 0.1 mole) and o-aminothiophenol (12.5 g, 0.1 mole) in toluene (200 ml) were refluxed under nitrogen. Water was collected in a Dean & Stark trap. Water evolution stopped after 6 hrs. when ca. 1.7 ml of water had collected. The solvents were removed on the rotary evaporator to yield a yellow oil. (7.62 g, 36%) Analysis found N=6.52%; S=14.64%. $C_{13}H_{11}NS$ requires N=6.57%; S=15.02%.

TABLE 1

PREPARATION AND TEST RESULTS OF BENZOTHIAZOLINE COMPOUNDS

| EXAMPLE No. | Benzo-thiazoline | o-amino-thiophenol Wt (g) | mol | Aldehyde/Ketone | wt. (g) | mol | Yield wt (g) | % | % N Found | Theory | % S Found | Theory | ROTARY BOMB (Mins) Mineral | Dioctyl |
|---|---|---|---|---|---|---|---|---|---|---|---|---|---|---|
| 1 | 2,2-bisethyl | 25 | 0.2 | Pentan-3-one | 17.2 | 0.2 | 34.1 | 88 | 6.86 | 7.25 | 16.30 | 16.58 | 100 | 273 |
| 2 | 2,2-dimethyl | 50 | 0.4 | propan-2-one | 58 | 1.0 | 60 | 91 | 8.211 | 8.48 | 20.09 | 19.39 | 123 | 372 |
| 3 | 2-methyl-2-ethyl | 25 | 0.2 | butan-2-one | 14.4 | 0.2 | 29.4 | 82 | 7.41 | 7.82 | 16.97 | 17.88 | 112 | 170 |
| 4 | 2-methyl | 50.0 | 0.4 | ethanal | 17.6 | 0.4 | 57.04 | 94 | 8.84 | 9.27 | 20.21 | 21.19 | 60 | 698 |
| 5 | 2-methyl-2-phenyl | 50.0 | 0.4 | acetophenone | 48.0 | 0.4 | 83.64 | 92 | 5.70 | 6.17 | 13.12 | 14.10 | 60 | 218 |
| 6 | 2-methyl-2-isobutyl | 50.0 | 0.4 | 4-methyl-pentan-2-one | 40.0 | 0.4 | 72.22 | 87 | 6.56 | 6.76 | 14.50 | 15.46 | 60 | 180 |
| 7 | 2,2-diphenyl | 25.0 | 0.2 | benzophenone | 36.4 | 0.2 | 53.54 | 93 | 4.55 | 4.84 | 11.09 | 11.07 | 80 | 673 |
| 8 | 2-propyl | 50.0 | 0.4 | propanal | 28.8 | 0.4 | 61.63 | 86 | 7.40 | 7.82 | 17.34 | 17.88 | 50 | 406 |
| 9 | 2-2-dibutyl | 22.0 | 0.18 | nonan-5-one | 25.0 | 0.18 | 45.45 | 91 | 5.20 | 5.62 | 12.30 | 12.85 | 56 | 197 |
| 10 | 2-isopropyl-2-methyl | 25.0 | 0.2 | 3-methyl-butan-2-one | 17.2 | 0.2 | 33.76 | 88 | 6.37 | 7.25 | 14.60 | 16.58 | 96 | 257 |
| 11 | 2-phenyl | 12.5 | 0.1 | benzaldehyde | 10.6 | 0.1 | 7.62 | 36* | 6.52 | 6.57 | 14.64 | 15.02 | 37 | — |
| 12 | 2-heptyl | 50.0 | 0.2 | octanal | 51.2 | 0.4 | 90.34 | 96 | 5.83 | 5.96 | 13.14 | 13.62 | 35 | 200 |
| 13 | 2-spiro-1'-cyclododecyl | 25.0 | 0.2 | cyclododecanone | 36.4 | 0.2 | 39.30 | 68 | 4.63 | 4.84 | 10.5 | 11.07 | 83 | 227 |
| 14 | 2-ethynyl-2- | 4.4 | 0.035 | but-3-yne-2-one | 2.38 | 0.035 | 5.90 | 80 | 7.92 | 8.80 | 21.5 | 18.29 | 20 | 330 |

TABLE 1-continued
PREPARATION AND TEST RESULTS OF BENZOTHIAZOLINE COMPOUNDS

| EXAMPLE No. | Benzothiazoline | o-aminothiophenol Wt (g) | mol | Aldehyde/Ketone | wt. (g) | mol | Yield wt (g) | % | % N Found | Theory | % S Found | Theory | ROTARY BOMB (Mins) Mineral | Dioctyl |
|---|---|---|---|---|---|---|---|---|---|---|---|---|---|---|
| 15 | methyl 2-(3-chloropropyl) 2-methyl | 12.5 | 0.1 | 5-chloropentan-2-one | 12.0 | 0.1 | 14.00 | 61 | 5.79 | 6.15 | 13.2 | 14.07 | 34 | 320 |
| 16 | 2-ethyl-2-phenylmethyl | 25 | 0-2 | 1-phenyl-butan-2-one | 29.6 | 0.2 | 44.00 | 86 | 4.67 | 5.49 | 11.60 | 12.55 | 17 | 90 |

*low yield due to spillage

TABLE 2
CORROSION INHIBITION AND METAL DEACTIVATION TESTS OF BENZOTHIAZOLINE COMPOUNDS

| EXAMPLE NO. | COMPOUND (for details of preparation see Example No.) | CONCENTRATION % by weight | RESULTS Test A | Test B |
|---|---|---|---|---|
| 17 | 2-ethyl-2-methylbenzothiazoline (3) | 1 | 2a | — |
| 18 | " | 0.1 | — | 2c |
| 19 | 2-methylbenzothiazoline (4) | 1 | 2a | — |
| 20 | " | 0.5 | — | — |
| 21 | " | 0.1 | — | — |
| 22 | 2-methyl-2-phenylbenzothiazoline (5) | 0.5 | — | 2a |
| 23 | " | 0.1 | — | 2a |
| 24 | 2-methyl-2-isobutyl benzothiazoline (6) | 1 | 1b | — |
| 25 | " | 0.5 | — | 3a |
| 26 | " | 0.1 | — | 3a |
| 27 | 2-propylbenzothiazoline (8) | 1 | 2a | — |
| 28 | " | 0.5 | — | 3a |
| 29 | " | 0.1 | — | 3a |
| 30 | 2,2-dibutylbenzothiazoline (9) | 1 | 1b | — |
| 31 | " | 0.5 | — | 3a |
| 32 | " | 0.1 | — | 3a |
| 33 | 2-methyl-2-isopropylbenzothiazoline (10) | 1 | 2a | — |
| 34 | " | 0.5 | — | 3a |
| 35 | " | 0.1 | — | 3a |
| 36 | 2-heptylbenzothiazoline (12) | 1 | 2a | — |
| 37 | " | 0.5 | — | 3a |
| 38 | " | 0.1 | — | 3a |

What is claimed is:

1. A composition comprising an oxidatively degradable constituent and an oxidation inhibiting amount of a benzothiazoline having the general formula:

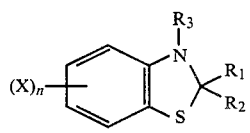

wherein $R_1$ and $R_2$ may be the same or different and may be a hydrogen atom, a hydrocarbyl group, a substituted hydrocarbyl group, an amino group or a halogen atom, a hydroxyl group, alkoxy or aryloxy group, or $R_1$ and $R_2$ together may form a cyclic group which may optionally contain a heterocyclic atom; $R_3$ is a hydrogen atom or a hydrocarbyl group; X is an optional substituent on the aromatic nucleus and where more than one substituent is present each may be the same or different and may be hydrocarbyl, halogen, hydroxyl, carboxyl, amino or amido or any other group which would not interfere with the antioxidant properties of the compound; alternatively two substituents may be taken together to form a polycyclic compound which may be substituted in like manner; n is zero or an integer of from 1 to 4.

2. A composition as claimed in claim 1 wherein the benzothiazoline has the formula

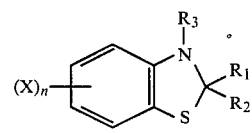

wherein X is absent or is an alkyl group containing from 1 to 20 carbon atoms, $R_1$ and $R_2$ may the same or different and selected from the group consisting of hydrogen atoms, alkyl groups containing 1 to 20 carbon atoms, aryl groups containing 6 to 10 carbon atom and alkaryl or aralkyl groups containing from 7 to 27 carbon atoms.

3. A composition as claimed in claim 1 wherein the benzothiazoline is present in amounts from 0.001 to 10% by weight of the total composition.

4. A composition as claimed in claim 3 wherein the benzothiazoline is present in amounts from 0.01 to 5% by weight of the total composition.

5. A composition as claimed in claim 4 wherein the benzothiazoline is present in amounts from 0.01 to 2% by weight of the total composition.

6. A composition as claimed in claim 1 wherein the oxidatively degradable constituent is a natural or synthetic carboxylate ester lubricant.

7. A composition as claimed in claim 1 wherein the oxidatively degradable constituent is a mineral or synthetic hydrocarbon oil.

8. A composition as claimed in claim 1 wherein the composition is a lubricating oil composition.

9. A composition as claimed in claim 1 wherein the composition is a hydraulic fluid composition.

10. A composition as claimed in claim 1 wherein the composition is a non-conducting electrical fluid.

11. A composition as claimed in claim 1 wherein the oxidatively degradable constituent is a polymer, rubber or plastic.

12. A method of inhibiting the oxidative deterioration of a composition which comprises adding an oxidation inhibiting amount of a benzothiazoline compound to a composition containing an oxidatively degradable constituent; said benzothiazoline compound having the general formula:

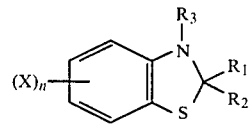

wherein $R_1$ and $R_2$ may be the same or different and may be a hydrogen atom, a hydrocarbyl group, a substituted hydrocarbyl group, an amino group or a halogen atom, a hydroxyl group, alkoxy or aryloxy group, or $R_1$ and $R_2$ together may form a cyclic group which may optionally contain a heterocyclic atom; $R_3$ is a hydrogen atom or a hydrocarbyl group; X is an optional substituent on the aromatic nucleus and where more than one substituent is present each may be the same or different and may be hydrocarbyl, halogen, hydroxyl, carboxyl, amino or amido or any other group which would not interfere with the antioxidant properties of the compound; alternatively two substituents may be taken together to form a polycyclic compound which may be substituted in like manner; n is zero or an integer of from 1 to 4.

* * * * *